United States Patent [19]

Rowe

[11] Patent Number: 4,930,499

[45] Date of Patent: Jun. 5, 1990

[54] SACRAL BRACE

[76] Inventor: Daniel G. Rowe, 2156 ROblyn, St. Paul, Minn. 55104

[21] Appl. No.: 311,338

[22] Filed: Feb. 16, 1989

[51] Int. Cl.⁵ .............................................. A61F 5/04
[52] U.S. Cl. ........................................ 128/78; 128/69
[58] Field of Search ............................ 128/78, 75, 69

[56] References Cited

U.S. PATENT DOCUMENTS

| | | | |
|---|---|---|---|
| 1,174,757 | 3/1916 | Packer | 128/78 |
| 1,562,935 | 11/1925 | Whisner | 128/78 |
| 2,100,964 | 11/1937 | Kendrick | 128/78 |
| 2,476,029 | 7/1949 | Dawson | 128/78 |
| 2,586,658 | 2/1952 | Hormann | 128/78 |
| 2,793,368 | 5/1957 | Nouel | 128/78 |
| 2,828,737 | 4/1958 | Hale | 128/78 |
| 3,094,984 | 6/1963 | Jewett | 128/78 |
| 3,351,053 | 11/1967 | Stuttle | 128/78 |
| 3,605,731 | 9/1971 | Tigges | 128/78 |
| 3,717,143 | 2/1973 | Johnson | 128/78 |
| 3,926,183 | 12/1975 | Spiro | 128/78 |
| 4,508,110 | 2/1985 | Modglin | 128/78 |
| 4,696,291 | 9/1987 | Tyo | 128/69 |

FOREIGN PATENT DOCUMENTS

| | | | |
|---|---|---|---|
| 2520537 | 11/1976 | Fed. Rep. of Germany | 128/75 |
| 3522535 | 1/1987 | Fed. Rep. of Germany | 128/69 |
| 1393798 | 2/1965 | France | 128/78 |

OTHER PUBLICATIONS

Orthopedic appliances Atlas, vol. 1, J. W. Edwards, Ann Arbor, Mich. 1952.

Primary Examiner—Edgar S. Burr
Assistant Examiner—Tonya Lamb
Attorney, Agent, or Firm—Palmatier & Sjoquist

[57] ABSTRACT

An improved comfortable extended wear sacral brace for supporting and binding the sacral iliac and lumbosacral joints comprised of a rigid posterior sacral pad with a vertical central channel. The sacral pad has padding adjacent the central channel. An abdominal leverage plate is provided for anchoring the sacral pad by means of sacral pad and abdominal plate tying straps. Leverage mechanisms with mechanical advantage linkages further connect the sacral pad and abdominal plate.

10 Claims, 6 Drawing Sheets

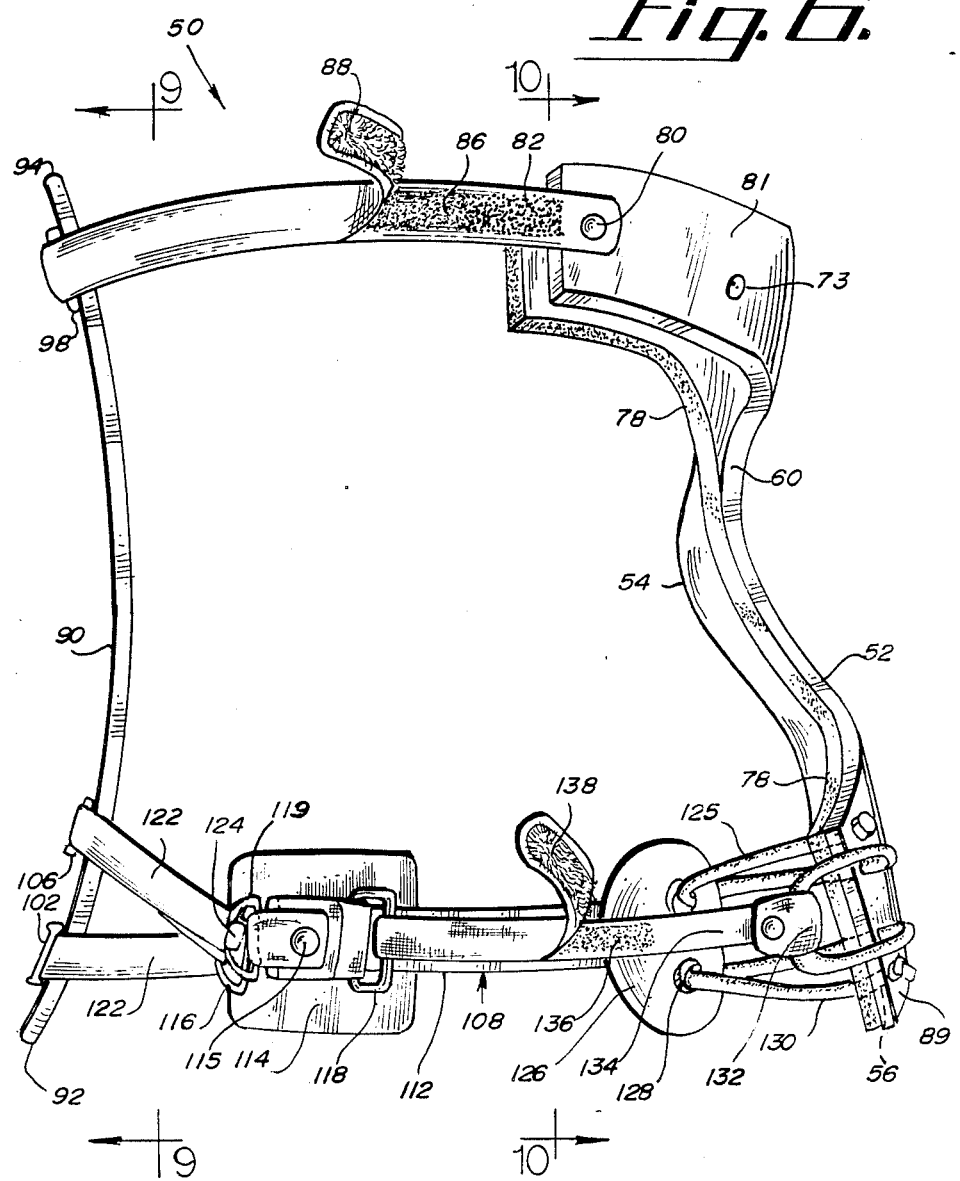

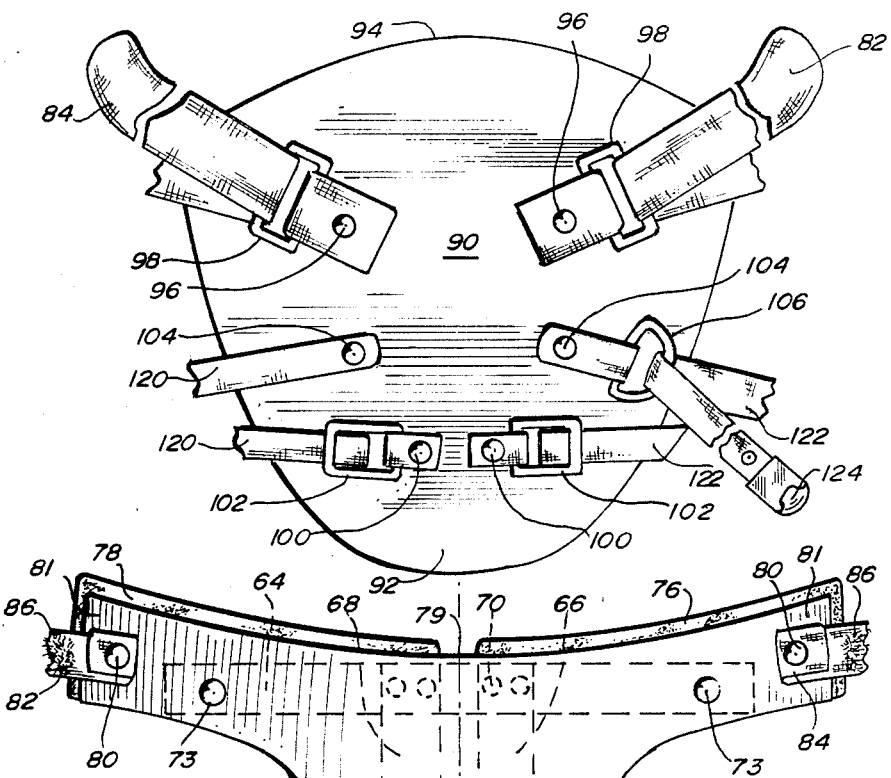
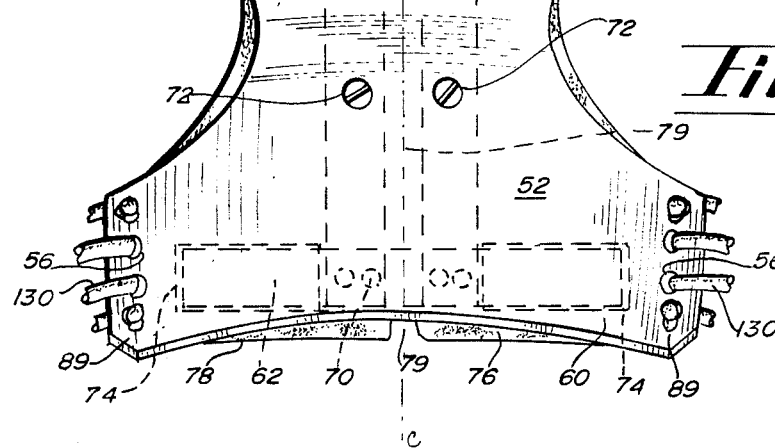

SACRAL BRACE

BACKGROUND OF THE INVENTION

This invention relates to a brace for the sacrum. The sacrum is part of the body or trunk, commonly know as the pelvis. Incapacitating pain will result should the sacrum come out of its normal alignment within the pelvis and in relation to the spine.

Referring to FIGS. 1-4, the detailed anatomy of the trunk or torso of a person may be viewed. The bony pelvis 10, which forms the base of the trunk, consists of two large innominate bones 12 with their two large wing-like ilia or iliac crests 14. The innominate bones 12 are joined in the front at the symphysis pubis 15. The upper most leg portions include the greater trochanters 13 which join the ilia 14 forming the hip joints.

The innominate bones 12 are joined in the back or posterior by the sacrum 16 which is the keystone of the spinal column 18 which includes 23 individual moveable vertebrae which are superimposed upon the sacrum 16. The bottom five vertebrae of the spine 18 are known as the lumbar vertebrae 20. The articulation between the fifth lumbar vertebrae 22 and the sacrum 16 is known as the lumbo-sacral joint 24. The sacrum 16 and innominate bones 12 are united by strong, wide ligaments to form the sacral-iliac joints 26. The tail bone is below sacrum 16 and is anatomically known as the coccyx 28.

Referring to FIGS. 4 and 5, the lumbar curve 30 appropriately may be seen which is a convex forward curve. An increase in this forward curve is known as lordosis 32.

When the sacrum has moved out of its normal alignment, incapacitating pain results immobilizing the injured person and requiring a brace to permit even minimal movement of the injured person.

Ligament strains of the sacral-iliac joints 26 and of the lumbo-sacral joint 24 are well known and cause excruciating and incapacitating back pain to an individual. Such strains are commonly caused by intra-abdominal pressures such as when an individual bends over and lifts an object incorrectly. Also there are other ways of injuring the sacral regions.

Braces are known for the sacrum which are typically made of flexible leather perhaps covered with felt and possibly reinforced with steel typically held in place with five straps of pliable leather. Such prior known braces provide a binding support for the pelvis; however, they are incapable of exerting any forces upon the sacral regions of the pelvis, are uncomfortable to the wearer and greatly restrict movement. Prior braces are also known to exert unnecessary forces on the spinous processes 19 which are the bony projections which extend posteriorly from the spinal column 18 and the sacrum 16.

There is a need for a sacral brace which exerts a force over the sacral regions of the pelvis 10 with an enhanced leverage mechanism that allows normal motion while massaging the lumbo-sacral and sacral-iliac regions as well as absorbing the shear forces between the brace and the pelvis which can be worn for extended time with comfort.

SUMMARY OF THE INVENTION

An improved comfortable extended wear sacral brace for supporting and binding the sacral-iliac and lumbo-sacral joints comprised of a rigid posterior sacral pad with a vertical central channel The sacral pad has padding adjacent the central channel. An abdominal leverage plate is provided for anchoring the sacral pad by means of sacral pad and abdominal plate tying straps. Leverage mechanisms with mechanical advantage linkages further connect the sacral pad and abdominal plate.

A principal object and advantage of the present invention is that it provides sacral support not heretofore known in a manner that is versatile and comfortable for extended wear and which is easy to put on and take off. The brace allows for normal motion of the hips and spine. Therefore, the brace is a dynamic brace which enables the individual wearing it to use it as a supporting device when doing normal activities that could cause further injury to the lumbo-sacral and sacral-iliac regions.

Another object and advantage of the present invention is that it provides for increased exerted forces upon the sacral-iliac and lumbo-sacral joints that are opposite to the forces that cause injury and pain. The sacral brace with its enhanced leverage mechanism prevents further injury, such as by lifting with the back flexed, and alleviates incapacitating pain from past strain or other injury to the sacrum.

Another advantage is that while the wearer moves about the sacral brace massages the lumbo-sacral and and sacral-iliac regions as it spreads its forces evenly over the sacral regions of the pelvis while yet providing for relief to the spinous processes of the spine and sacrum.

Another advantage and object of the present invention is that it readily permits air circulation about the lumbo-sacral and pelvic regions of the body making the brace more comfortable for extended wear.

Still another principal object and advantage of the present invention is that it absorbs shear forces between the brace and pelvic regions as the pelvis moves up and down and rotates 5° when a wearer moves about permitting comfortable extended wear as the wearer stands, walks, sits or performs other normal functions.

BRIEF DESCRIPTION OF THE DRAWINGS

FIG. 6 is a side elevation view of the sacral brace of the present invention;
FIG. 7 is a rear elevation view of the rigid sacral pad of the sacral brace;
FIG. 8 is a front elevation view of the abdominal leverage plate.

DETAILED SPECIFICATION

Figure 1:
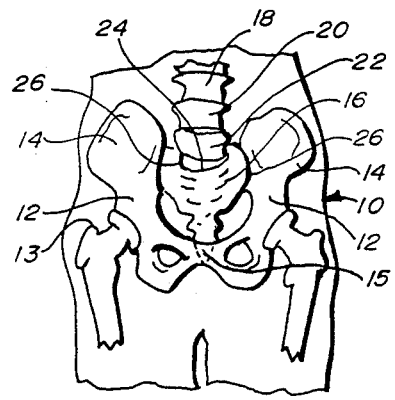
FIG. 1 is anterior or front view of the pelvis.
Figure 2:
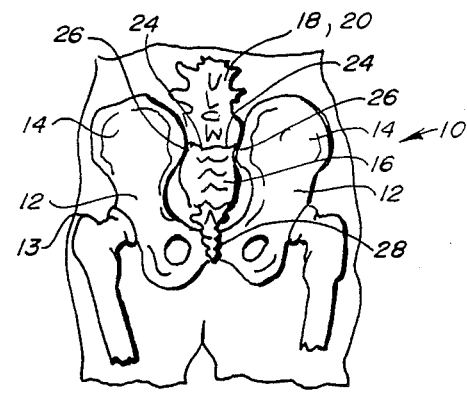
FIG. 2 is a posterior or rear view of the pelvis.
Figure 3:
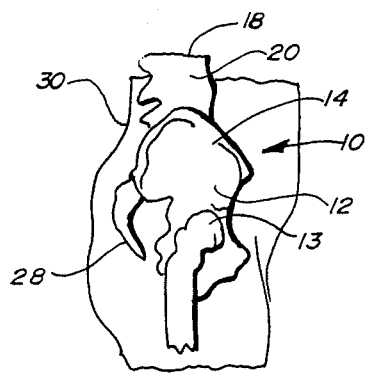
FIG. 3 is a lateral or side view of the pelvis.
Figure 4:
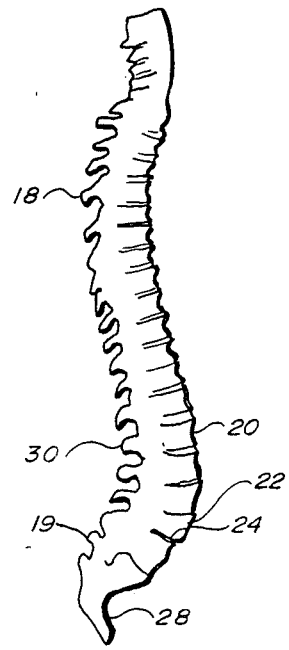
FIG. 4 is a lateral or side view of the spinal column.
Figure 5:
FIG. 5 is a lateral or side view of a person.
Figure 11:
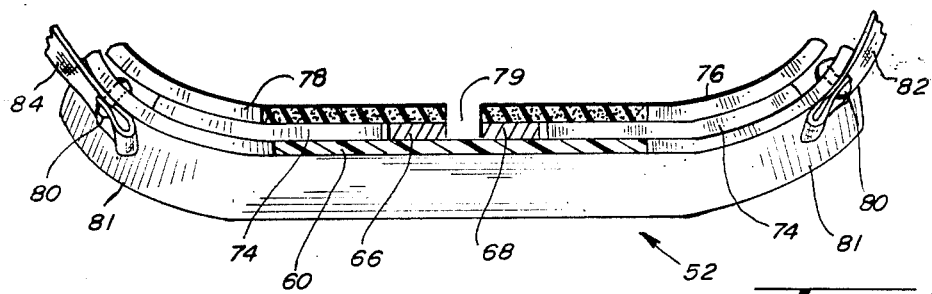
FIG. 11 is a view taken along lines 11—11 of FIG. 10.
Figure 9:
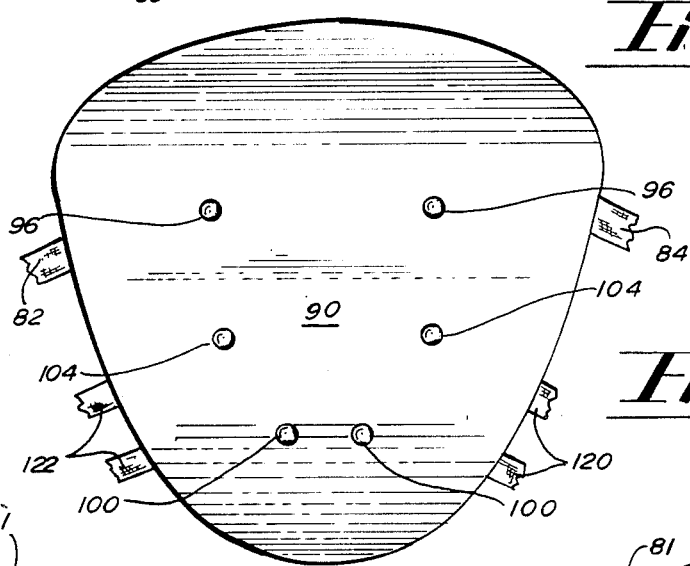
FIG. 9 is a view taken along lines 9—9 of the FIG. 6.
Figure 10:
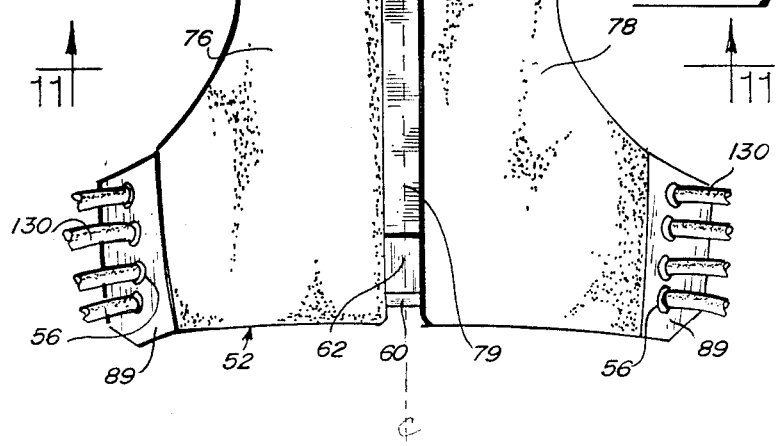
FIG. 10 is a view taken along lines 10—10 of FIG. 6.

Referring to FIGS. 6-11, the detail structure of the sacral brace 50 of the present invention may be seen. The sacral brace 50 generally comprises a rigid sacral pad 52 which has right padding 76 and left padding 78 adjacent the vertical channel 79. Plate and pad tying straps 82 and 84 connect the sacral pad 52 to the abdominal leverage plate 90. Leverage mechanisms 108 and 109 also connect the abdominal leverage plate 90 to the rigid sacral pad 52 each which further includes mechanical advantage linkages 125.

When the sacrum 16 has moved rearwardly or posteriorly out of its normal joint alignment, an extension brace (FIGS. 6–13) tends to force the sacrum 16 back into proper alignment. When the sacrum 16 has moved inwardly, forwardly or anteriorly out of its normal joint alignment, a flexion brace (FIG. 14) will exert a force on the lumbar vertebrae 20 which tends to force the lumbo-sacral joint back into proper alignment.

More specifically, the rigid sacral pad 52 of the extension model of sacral brace 50 has a lumbo-sacral curve 54 to readily contorm with the lumbar curve 30 of the spine 18 as it pushes inwardly on the lumbo-sacral and sacral-iliac regions. Pad 52 preferably has four eyelets 56 on each of its distal lower lateral projecting portions 89 in the outer plastic mounting plate 60. Plate 60 suitably may be made out of polypropylene or other rigid plastic.

Rigidity is further added to mounting plate 60 by lower horizontal convex metal band 62, upper horizontal concave metal band 64, right convex metal upright 66 and left convex metal upright 68, all suitably made of aluminum or other light weight metal. Bands 62 and 64 and uprights 66 and 68 are suitably fastened together by rivets or fasteners 70, 72 and 73.

Appropriately, plastic spacers 74 lie along portions of horizontal metal bands 62 and 64 to permit flush or even mounting of the right padding 76 and the left padding 78, suitably by glue or the like. Padding 76 and 78 may be made of foam rubber or the like which readily absorbs shear forces, provides for uniform pressure or forces and massages the sacral regions during movement of the wearer.

Vertical channel 79 lies along center line C between and adjacent the right padding 76 and the left padding 78. Channel 79 permits air circulation therethrough and provides for pressure-free relief of the pad upon the spinous process 19.

Left plate and pad tying strap 82 and right plate and pad tying strap 84 are appropriately fastened to the upper lateral and distal projecting portions 81 of pad 52 by fasteners 80. Straps 82 and 84 have complementary VELCRO™ pile or loop material 86 and VELCRO™ hooks 88 there along as shown to permit straps 82 and 84 to be securely fastened between sacral pad 52 and leverage plate 90 by appropriately laying straps 82 and 84 back upon themselves after interconnecting pad 52 and plate 90.

The rigid sacral pad 52 has additional open regions between upper projecting portions 81 and lower projecting portions 89, as well as vertical channel 79, to readily permit air circulation about the sacral pad 52.

Although the rigid sacral pad 52 appropriately is constructed of the above mentioned components, it is believed in mass production or manufacture the sacral pad 52 could be molded of thick rigid plastic or other suitable material without bands 62 and 64, uprights 66 and 68 and spacers 74. However, one must consider that sacral pad 52 be appropriately sized for the wearer.

Abdominal leverage plate 90 is rigid and appropriately made of polypropylene or the like having an outwardly curved lower portion 92 and outwardly curved upper portion 94. A pair of upper fasteners 96 appropriately support rings or loops 98. In fitting the sacral brace 50, the tying straps 82 and 84 are directed to pass through rings 98 and then be pressed back upon themselves to secure the upper lateral projecting portions 81 of sacral pad 52 to the upper portion 94 of abdominal leverage plate 90. As such, straps 82 and 84 are a quick release connecting means which may be embodied in other forms.

The leverage plate 90 also has a pair of like or similar lower fasteners 100 which appropriately support like buckles 102 permitting adjustable connection of straps 120 and 122 to plate 90. Leverage plate 90 also has a pair of similar intermediate like fasteners 104. However, right fastener 104 fastens the end of strap 120 while left fastener 104 appropriately supports a ring or loop 106 through which left strap 122 may pass through. Strap 122 supports a hook 124 at its other end.

Figure 12:
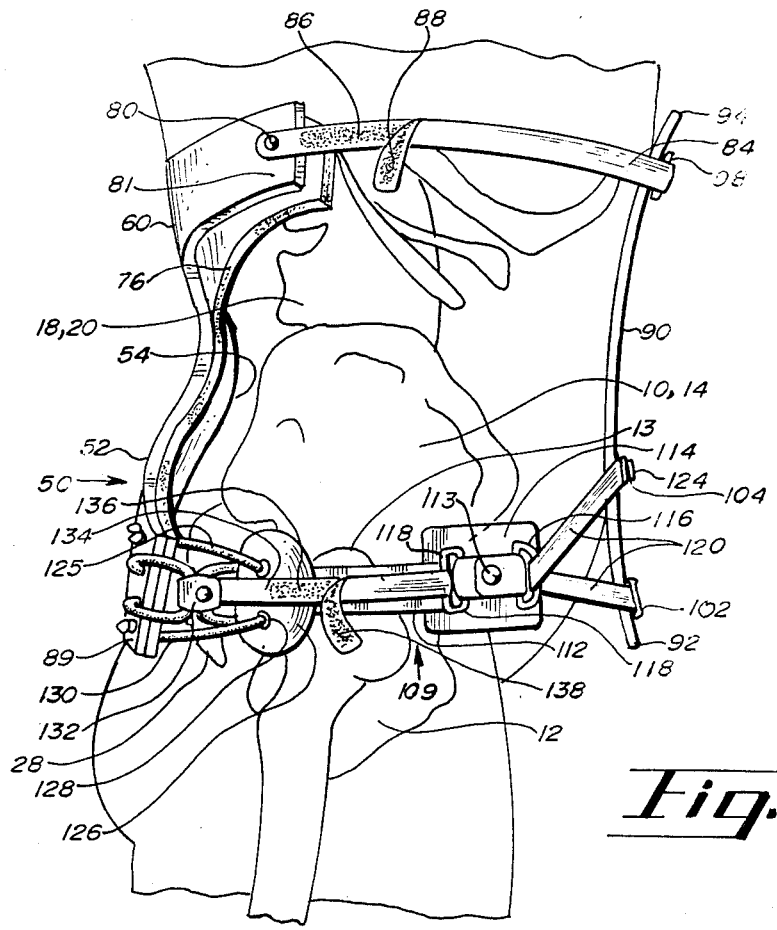
FIG. 12 is a lateral or side view of the sacral brace on a wearer.

Left and right leverage mechanisms 108 and 109 appropriately connect the lower lateral projecting portions 89 of sacral pad 52 and lower portion 92 of leverage plate 90. Left and right leverage mechanisms 108 and 109 are essentially mirror images of each other as seen in FIGS. 6 and 12 with the exception that left leverage mechanism 108 (FIG. 6) supports two front or forward rings 116 and 119 while right leverage mechanisms 109 (FIG. 12) supports only one front ring 116.

Leverage mechanisms 108 and 109 suitably include left and right mounting strips 112 suitably made of plastic. Strips 112 appropriately have padding 114 at their forward ends. Left mechanism 108 and padding 114 support front rings 116 and 119 and back ring 118 by fastener 115. Right strip 112 and padding 114 appropriately support single forward ring 116 and back ring 118 by fastener 113.

Right side forward strap 120 is appropriately connected to fastener 104 and directed through front ring 116 of mounting strip 112 and then back to and through buckle 102 which renders mounting strap 120 adjustable.

Left side forward strap 122, which is quickly releasable and adjustable, adjustably originates at left buckle 102 and passes through front ring 116 of left mounting strip 112 through left ring or loop 106 and back to second forward ring 119 where hook 124 is releasably connected.

Identical left and right mechanical advantage linkages 125 include eyelet plate 126 with eyelets 128 located rearwardly therein. Left and right plates 126 are appropriately mounted on and at the rear ends of strips 112. Strong strings 130 are appropriately threaded through eyelets 56 of lower lateral projecting portions 89 of sacral pad 52 and back through eyelets 128 of eyelet plate 126 as well as through the looped end 132 of adjustable rear straps 134 as shown in FIGS. 6 and 12. Rear straps 134 each have VELCRO™ pile or looped material 136 with complementary VELCRO™ hook material 138 to permit rear straps 134 to be folded and secured back upon themselves after the strap 134 have been tightened. This arrangement gives a two-to-one mechanical advantage to linkages 125.

Figure 13:
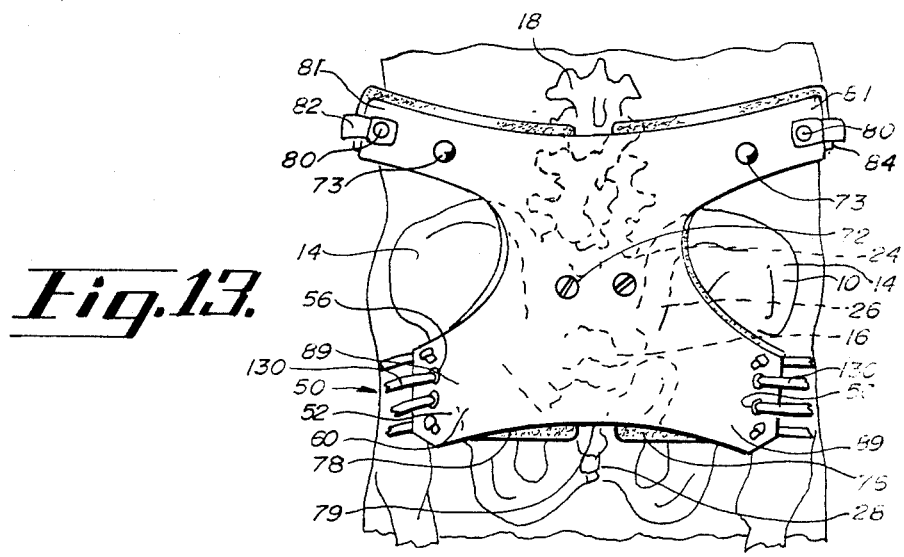
FIG. 13 is a posterior or rear view of the sacral brace on a wearer.

Referring to FIGS. 12 and 13, the fitting on the wearer and operation of sacral brace 50 is explained and observed. Initially, rigid sacral pad 52 and abdominal leverage plate 90 are positioned on the wearer with right plate and pad tying strap 84 and right side leverage mechanism 108 already connecting both pad 52 and plate 90. Thereafter, the wearer may thread left plate and pad tying strap 82 through ring or loop 98 and snugly tension both left and right straps 82 and 84 to a comfortably snug fit.

Next, the wearer grasps left side forward strap 122 which is directed to pass through forward ring 116, ring 106 at left intermediate fastener 104 on plate 90 and finally with hook 124 being connected to second forward ring 119. Now both pad 52 and plate 90 are now fully connected and leverage mechanisms 108 with mechanical advantage linkages 125 may be appropriately adjusted.

It is appropriate to simultaneously grasp left and right rear straps 134 of mirror image left and right mechanical advantage linkages 125 and pull them rearwardly which will pivot pad 52 on curve portion 54 to exert strong forces inwardly upon the sacrum 16. Thereafter, straps 1 be laid upon themselves to suitably interlock VELCRO TM pile material 136 and VELCRO TM hook material 138 completing the fitting of sacral brace 50. Removal of brace 50 appropriately follows this procedure in reverse.

Figure 14:
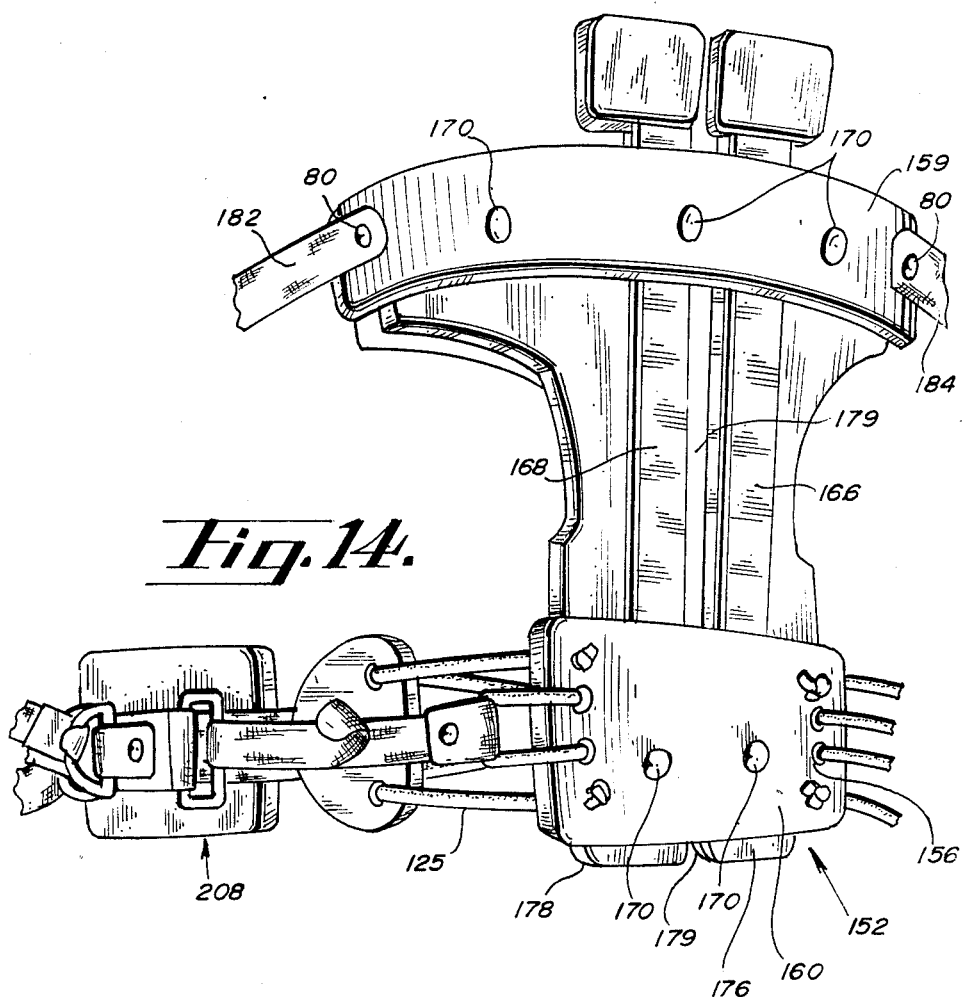
FIG. 14 is a modified embodiment of the sacral brace.

FIG. 14 shows a modified or second embodiment of rigid sacral pad 152 which is nearly the same as pad 52 without the lumbo-sacral curve 54 of pad 52. Sacral pad 152 is appropriately called the flexion model suitable for various strains and injuries to the pelvic region wherein the sacrum 16 has become misaligned inwardly or anteriorly. Sacral pad 152 forces the lumbar vertebrae 20 and 22 into alignment with the sacrum 16.

Modified sacral pad 152 appropriately has eyelets 156, upper plastic mounting plate 159, lower plastic mounting plate 160, lower horizontal convex metal band (not shown) and upper metal convex band (not shown). Similarly, right and left metal uprights 166 and 168 are provided which permit fasteners or rivets 170 to appropriately mount and interconnect plastic spacers (not shown), right padding 176 and left padding 178. Modified sacral pad 162 appropriately has vertical channel 179. Modified sacral pad 152 appropriately has leverage mechanisms 208 with mechanical advantage linkages 125 as in preferred embodiment 50.

The present invention may be embodied in other specific forms without departing from the spirit or essential attributes thereof, and it is therefore desired that the present embodiment be considered in all respects as illustrative and not restrictive, reference being made to the appended claims rather than to the foregoing description to indicate the scope of the invention.

What is claimed:

1. An improved extended wear sacral brace for supporting and binding the sacro-iliac and lumbo-sacral joints which has a leverage mechanism and which spreads its exerted forces over the sacral regions, massages the lumbo-sacral and sacro-iliac regions, absorbs shear forces between the brace and pelvis, provides relief for boney spinous processes and permits air circulation about the lumbo-sacral and pelvic regions of the body, comprising
    (a) a rigid posterior sacral pad with upper and lower lateral projecting portions with open regions therebetween for air circulation, a vertical central channel for spinous processes relief and air circulation and left and right padding on the pad adjacent the central channel which makes the brace wearable, for extended wear, spreads the pad's exerted forces over the sacral regions, absorbs shear forces between the brace and pelvis and together with the pad massages the lumbo-sacral and sacro-iliac regions;
    (b) an abdominal leverage plate for anchoring the sacral pad with upper and lower portions each curving outwardly from the wearer's abdomen to permit extended wear of the brace as the wearer walks, stands and sits;
    (c) left and right sacral pad and abdominal plate tying straps for connecting either of the two corresponding upper or lower portions of the sacral pad and abdominal plate, and
    (d) left and right leverage mechanisms for connecting the other of the two corresponding upper or lower portions of the sacral pad and abdominal plate and for permitting the sacral pad to exert its forces and massage the lumbo-sacral and sacral-iliac regions.

2. The sacral brace of claim 1 wherein the rigid posterior sacral pad has a lumbo-sacral posterior curve to further exert force on the sacrum and utilize the sacrum as a fulcrum.

3. The sacral brace of claim 1 wherein the tying straps connect the respective upper portions of the sacral pad and abdominal plate while the leverage mechanisms adjustably connect the respective lower portions of the sacral, pad and abdominal plate to forceably pivot the sacral pad's curve inwardly upon the sacrum.

4. The sacral brace of claim 1 wherein the sacral pad is of integrally molded plastic.

5. The sacral brace of claim 1 wherein the sacral pad is comprised of a plastic mounting plate with curved metal bands and uprights mounted on the mounting plate.

6. The sacral brace of claim 1 wherein the padding is foam rubber.

7. The sacral brace of claim 1 wherein the leverage mechanisms each include a two-to-one mechanical advantage linkage.

8. The sacral brace of claim 1 wherein the leverage mechanisms each further comprise
    (i) a mounting strip;
    (ii) a forward strap connecting the strip to the corresponding portion of the abdominal plate; and
    (iii) A two-to-one mechanical advantage linkage connecting the strip to the corresponding portion of the sacral pad.

9. The sacral brace of claim 1, wherein the vertical central channel is open from top to bottom for air circulation.

10. An improved extended wear sacral brace for supporting and binding the sacro-iliac and lumbo-sacral joints which has a leverage mechanism and which spreads its exerted forces over the sacral regions, massages the lumbo-sacral and sacro-iliac regions, absorbs shear forces between the brace and pelvis, provides relief for boney spinous processes and permits air circulation about the lumbar, sacral and pelvic regions of the body, comprising
    (a) a rigid posterior sacral pad with upper and lower lateral projecting portions with open spaces therebetween for air circulation, an open vertical central channel for spinous processes relief and air circulation, a lumbo-sacral posterior curve and left and right foam rubber padding on the pad adjacent the central channel which makes the brace wearable for extended wear, spreads the pads exerted forces over the sacral regions, absorbs shear forces between the brace and pelvis and together with the pad massages the lumbo-sacral and sacro-iliac regions;

(b) an abdominal leverage plate with upper and lower portions each which curve outwardly from the wearer's abdomen to permit extended wear of the brace as the wearer walks, stands and sits, the plate being for anchoring the sacral pad;

(c) left and right sacral pad and abdominal plate tying straps for connecting the two corresponding upper portions of the sacral pad and abdominal plate, one strap being of a releaseable construction, and (d) left and right leverage mechanisms for connecting the two corresponding lower portions of the sacral pad and abdominal plate, for forceably pivoting the sacral pad's curve inwardly upon the sacrum and for permitting the sacral pad to exert its forces and massage the lumbo-sacral and sacral-iliac regions, one mechanism being of a releaseable construction while each mechanism comprises:

(i) a mounting strip;

(ii) a forward strap connecting the strip to the corresponding portion of the abdominal plate; and (iii) A two-to-one mechanical advantage linkage connecting the strip to the corresponding portion of the sacral pad.

* * * * *

UNITED STATES PATENT AND TRADEMARK OFFICE
CERTIFICATE OF CORRECTION

PATENT NO.   : 4,930,499

DATED        : June 5, 1990

INVENTOR(S)  : Daniel G. Rowe,

It is certified that error appears in the above-identified patent and that said Letters Patent is hereby corrected as shown below:

Column 3, line 17, delete "contorm" and insert --conform--.

Column 5, line 16, delete the numeral "1" and insert --134--.

Column 5, line 63, delete the "," after the word "wearable".

Signed and Sealed this

Sixteenth Day of July, 1991

Attest:

HARRY F. MANBECK, JR.

*Attesting Officer*         *Commissioner of Patents and Trademarks*